United States Patent [19]
Rausnitz

[11] Patent Number: 5,639,424
[45] Date of Patent: Jun. 17, 1997

[54] PORTABLE FERTILITY TESTER

[76] Inventor: Gerald J. Rausnitz, Box 549, Remsenberg, N.Y. 11960

[21] Appl. No.: 555,360

[22] Filed: Nov. 8, 1995

[51] Int. Cl.⁶ ............................ G01N 21/84; G01N 21/00
[52] U.S. Cl. .................. 422/61; 435/305.2; 436/809; 436/814; 436/906
[58] Field of Search ................ 422/61; 435/305.3, 435/305.2, 288.4; 359/398, 396; 436/808–809, 814, 906

[56] References Cited

U.S. PATENT DOCUMENTS

| | | | |
|---|---|---|---|
| 2,041,290 | 5/1936 | Jackson | 359/398 |
| 2,899,046 | 8/1959 | Cox | 359/398 |
| 4,333,908 | 6/1982 | Maki et al. | 422/61 |
| 4,976,923 | 12/1990 | Lipsky et al. | 422/61 |
| 5,062,697 | 11/1991 | Mitchell | 359/398 |
| 5,149,501 | 9/1992 | Babson et al. | 422/61 |
| 5,429,804 | 7/1995 | Sayles | 422/61 |

*Primary Examiner*—Lyle A. Alexander
*Attorney, Agent, or Firm*—Levine & Mandelbaum

[57] ABSTRACT

A portable fertility tester for identifying days during the menstrual cycle when a woman is most likely to conceive has a circular disc, with transparent regions indexed to each of the days of the cycle, rotatably mounted within a housing and cover. The housing and cover form a window for exposing a transparent region on the disc for depositing a saliva specimen. An ocular is provided with a magnifying lens for examining the appearance of the saliva which is indicative of fertility, and a light emitting diode is provided for backlighting the specimen during examination. The cover may be removed to allow replacement of the disc for each menstrual cycle.

5 Claims, 3 Drawing Sheets

PORTABLE FERTILITY TESTER

BACKGROUND OF THE INVENTION

This invention relates to devices for determining whether a woman is at a time in her menstrual cycle when she is likely to conceive. More specifically, the invention is directed to the construction of such an apparatus which is portable, inexpensive, easy to use, and which can be employed by a woman to evaluate her fertility on any day in her menstrual cycle without the intervention of a physician or other health professional.

It is known that there are some days in a woman's menstrual cycle when she is fertile and likely to conceive and other days when conception is improbable. The fertility period typically lasts approximately six days out of each thirty day period. It is known in the art to measure a woman's body temperature to detect fertile times. A decrease in temperature is associated with the fertile portion of the cycle. Another method of determining fertility is by the consistency of the mucus in the vagina. Viscosity of the mucus increases when fertility is high.

Still another technique for determining fertility is by visual examination of the woman's saliva. At fertile times, microscopic viewing of the saliva reveals a structure which resembles ferns. At infertile times, the same inspection of the saliva reveals dotted structures. Examination of saliva offers a simple way to determine fertility.

It is known in the art to assemble a slide and magnifier into a cylindrical tube having a source of illumination. Such a device is disclosed in Czech Patent No. 23701 entitled "Fertility Tester" issued to Meopta Prerov A.S. on an application made on Jun. 23, 1992 and published on Oct. 20, 1992. In addition to the inconvenience of having to clean such a device of the prior saliva sample before each use, the Czech device does not enable a comparison of the saliva specimens from day to day nor a comparison of specimens between days in different months.

SUMMARY OF THE INVENTION

The aforementioned problems of the prior art are overcome by the instant invention which provides for a fertility tester including a circular disc having a concentrically disposed plurality of at least partially transparent regions, support means, in the form of a housing in which the disc is rotatably mounted, and masking means in the form of a cover mounted on the housing and covering a portion of the disc thereby preventing viewing of some of the transparent regions, the masking means further having a window for exposing at least one transparent region on which a woman may deposit a specimen of her saliva, the disc being rotatable relative to the housing whereby any one of the transparent regions may be exposed. The cover, additionally, has an ocular for viewing one of the disc transparent regions under magnification. Illumination means are mounted in the housing for back lighting the saliva on the disc. The disc is imprinted with an identifying indicium for each of the transparent regions. The cover has an aperture for exposing the indicium corresponding the transparent region under view.

It is therefore an object of the invention to provide a fertility tester which enables a woman to readily view her saliva with magnification under back light.

Another object of the invention is to provide a fertility tester which is inexpensive, portable and easily carried on the person.

Still another object of the invention is to provide a fertility tester wherein salvia patterns for the days of a complete menstrual cycle can be stored and viewed.

A further object of the invention is to provide a fertility tester with a self extinguishing light source.

Other and further objects of the invention will be apparent from the following drawings and description of a preferred embodiment of the invention in which like reference numerals are used to indicate like parts in the various views.

DESCRIPTION OF THE PREFERRED EMBODIMENT

Figure 1:
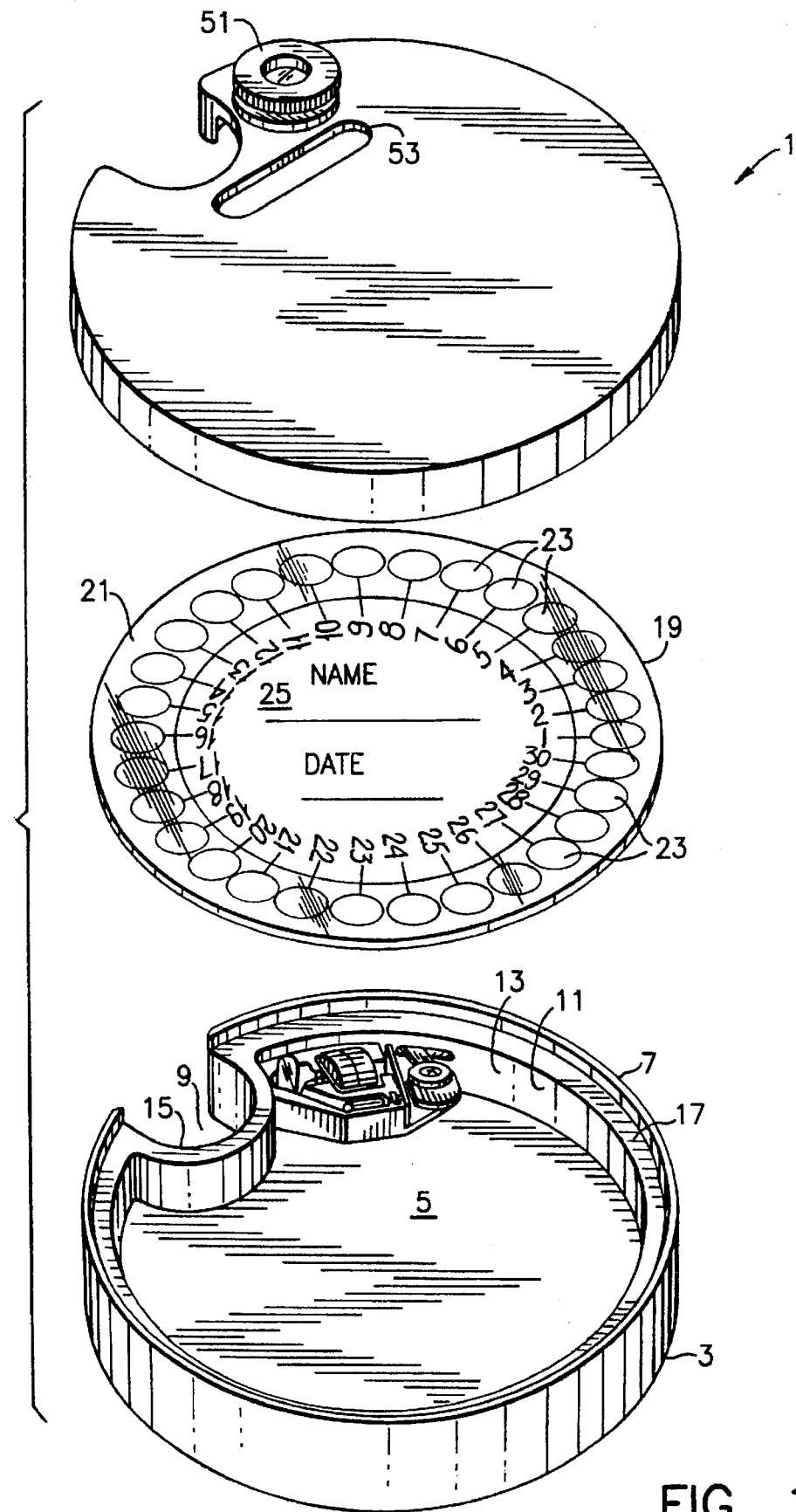
FIG. 1 is an exploded perspective view of a portable fertility tester in accordance with the preferred embodiment of the invention.

Referring now to FIG. 1 of the drawings there is shown a fertility tester 1 having a lower, generally cylindrical, housing 3 with a floor 5 and a cylindrical wall 11. The wall 11 extends upwardly from the floor 5 and has a reverse curvature 15 so as to form a notch in the circumference of the otherwise circular housing 3. The top of the wall 11 is stepped, having an inwardly extending ledge 17 from which there upwardly extends a cylindrical lip 7 having an outer circumference flush with the outer circumference of the wall 11.

Seated on the ledge 17 is a circular disc 19 having a circumferential track 21 along which there are closely spaced circular transparent regions 23. The disc 19 may be made of a plastic or glass material. If the disc 19 is made of a transparent material, the transparent regions 23 may be defined by imprinting borders surrounding each of the transparent regions 23 on the disc 19 as shown in the drawings. If the disc is formed from an opaque material, the transparent regions 23 may be provided by forming apertures in the disc and mounting a transparent slide in each aperture. Each of the circular regions 23 of the transparent disc 19 serves as a slide for receiving the saliva of the user on a given day.

Adjacent each circular transparent region is an indicium in the form of an index number corresponding to the day in the cycle during which the saliva is been examined to determine fertility. A data area 25 is provided in the central region of the disc 19 for recording the name of the user and a date, e.g., corresponding to the first day of the cycle recorded on the disc 19. Each disc 19 is preferably provided with thirty circular transparent regions 23 to encompass the length of most typical menstrual cycles.

Imprinted on the disc 19 are the indicia in the form of index numbers arranged in a circle inside and concentric with the track 21 in which the transparent regions 23 are disposed. Each indicium or index number is in radial alignment with a corresponding circular transparent region 23 and radial lines extend between the indicia and circular transparent regions 23 to indicate the correspondence.

Figure 2:
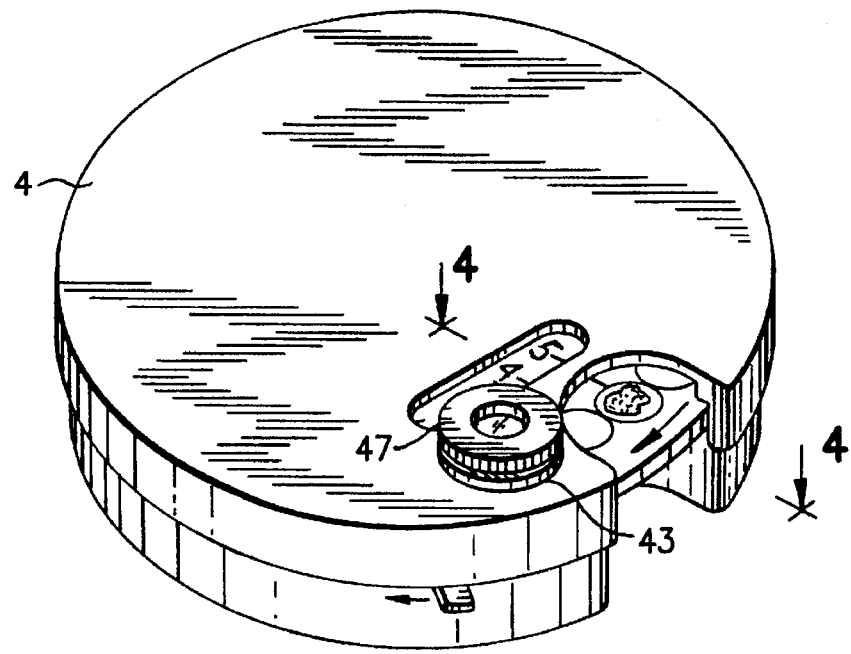
FIG. 2 is a perspective view of a portable fertility tester in accordance with the preferred embodiment of the invention in a first disposition.
Figure 3:
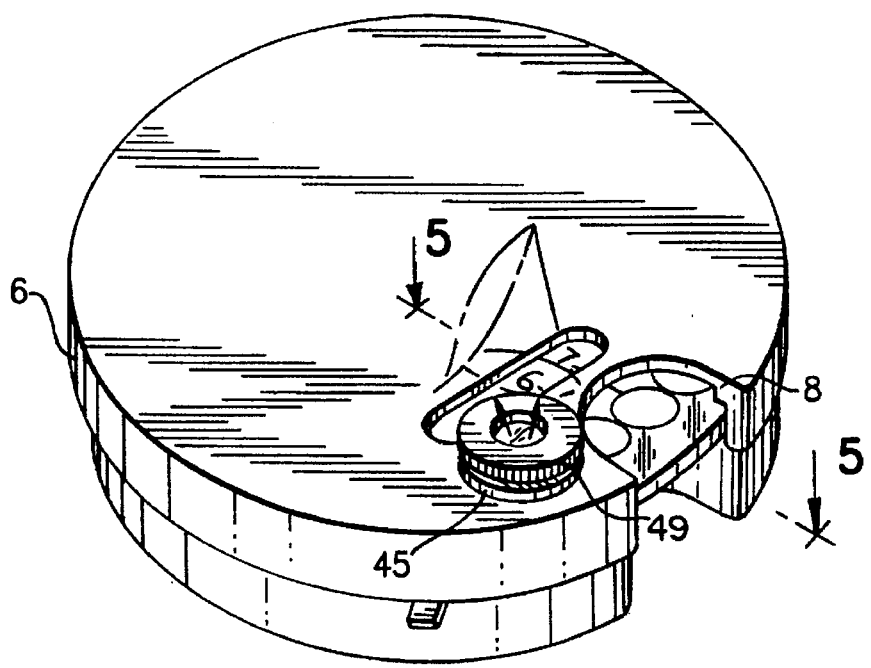
FIG. 3 is a perspective view of a portable fertility tester in accordance with the preferred embodiment of the invention in a second disposition.

The outer diameter of the disc 19 is just slightly less than the inner diameter of the lip 7 on the housing 3 but greater than the inner diameter of the wall 11. When seated atop the ledge 17, the disc 19 is free to rotate about its center while confined against translational movement by the lip 7. Referring to FIGS. 2 and 3, as the disc 19 is rotated, the circular transparent regions 23 are within the radius of the wall 11, except at the notch 9 whereat the disc 19 extends beyond the reverse curvature 15 in the wall 11, thereby making a circular transparent region 23 accessible for deposit of a saliva specimen, as well as for viewing if desired.

Figure 4:
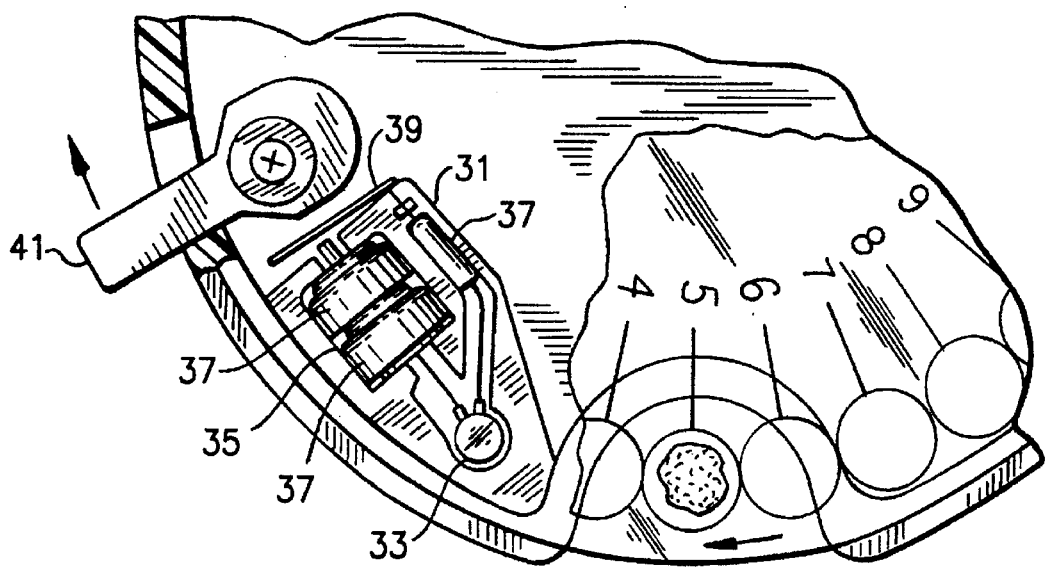
FIG. 4 is a sectional plan view of a portable fertility tester in accordance with the preferred embodiment of the invention taken along line 4—4 of FIG. 2.
Figure 5:
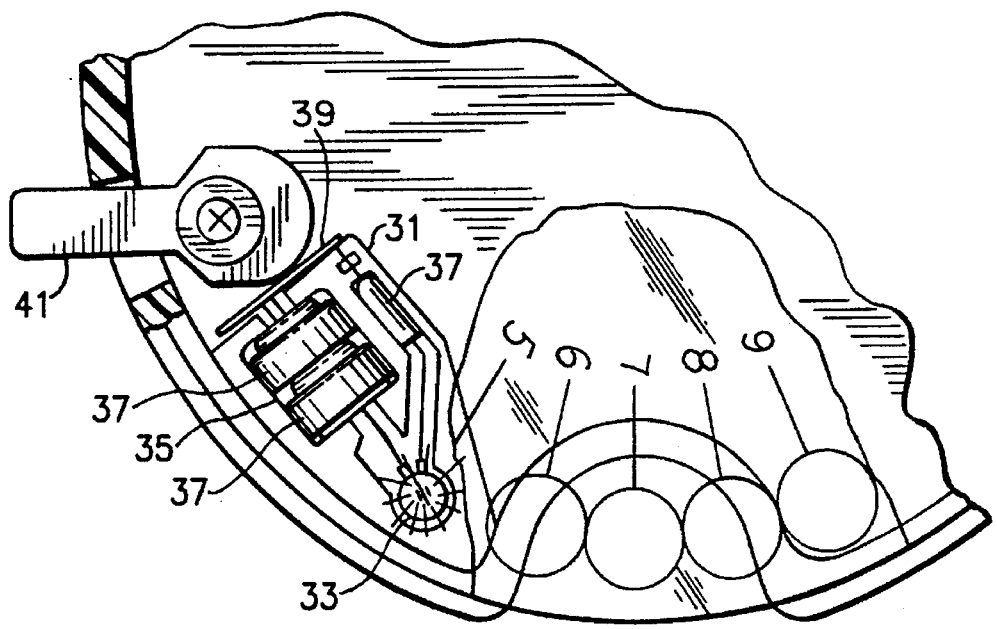
FIG. 5 is a sectional plan view of a portable fertility tester in accordance with the preferred embodiment of the invention taken along line 5—5 of FIG. 3.

As best seen in FIGS. 4 and 5, within the housing 3 there is mounted an illumination unit 31 in the form of a light emitting diode (LED 33) having a battery compartment 35 for receiving two conventional button cells. The LED 33 is connected by a conductor, through a resistor 37 to a contact of a normally open switch 39 actuated by a lever cam 41. When the switch 39 is actuated (see FIG. 5), it applies the voltage from the batteries to the LED 33 thereby causing the LED 33 to light.

Removably mounted on top of the housing 3 is a cover 4 which serves as a mask for obscuring most of the upper surface of the disc 19 while permitting access or viewing of a specimen and its identifying indicium for a selected day. The cover 4 has a cylindrical wall 6 with an inner diameter equal to or only slightly greater than the outer diameter of housing wall 11 so that the cover 4 can be removably mounted on the housing 3 and held in place by friction between the cover wall 6 and housing outer wall 11. The cover 4 and housing 3 are preferably fabricated from a substantially rigid plastic material having some resilience to facilitate placement and removal of the cover 4 on the housing 3 and to enhance friction between the them.

The otherwise circular cover 4 has a notch 8 in registration with the notch 9 in the housing wall 11, the notches 8 and 9 in the cover 4 and housing 3, respectively, defining an open window 10 through which the track 21 passes as the disc 19 is rotated about its center, thereby permitting access to any circular transparent region of the disc 19 for enabling a specimen of saliva to be deposited thereon (see FIGS. 2 and 3).

Within the top surface of the cover 4, adjacent the notch 8, there is a circular aperture in which there is mounted a cylindrical boss 43 having a threaded bore. An ocular 45 has a threaded focusing tube with threads on its outer circumference and a magnifying lens 31 at its upper end surrounded by a collar 47. The focusing tube of the ocular 45 is threaded into the bore in the boss 43. Molded into the outer circumference of the collar 47 of the ocular 45 are axial grooves 49 to enhance grasping of the collar 47 for rotating the ocular to focus a magnified image of the saliva on the transparent region 23 of the disc 19 in registration with the ocular 45 which is back lit when the lever cam 41 of switch 39 is actuated.

Formed in the upper surface of the cover 4 adjacent the notch 8 and ocular 45 is an elongated slot 53 in alignment with the indicia imprinted on the disc 19 for enabling the index number of each circular transparent region 23 on the disc 19 to be seen when it is in position for deposit of a saliva specimen at the window 10 or in alignment with the ocular 45 for viewing.

In use, woman seeking to determine if she is in the fertile time of her menstrual cycle rotates the disc 19 until the numbered disc transparent region 23 corresponding to the day of her menstrual cycle is positioned within the widow 10. She then applies a small amount of her saliva to the exposed surface of the transparent region 23 and allows it to dry for from one to five minutes. Thereafter, the disc 19 is rotated until the transparent region 23 for that day is in alignment with the ocular 45. The switch 39 can then be activated to illuminate the specimen on the disc transparent region 23. The fertility tester is then held with the lens 51 close to the eye.

The ocular 45 is focused by rotating the collar 47 until a clear pattern can be seen in the saliva. If the pattern is fern-like, the woman may conclude that she is fertile. If a dot pattern is seen, then it may be concluded that she is not likely to be fertile at the present time. The same procedure is repeated daily throughout the menstrual cycle. At the end of each cycle, the disc 19 may be replaced with another one by removing the cover 4 from the housing 3 and simply lifting the disc 19 out. Data indicative of the name of the user and month of the cycle may be recorded on the disc 19 for later reference.

The saliva patterns which indicate fertility are known in the art and are not part of the invention which is directed to apparatus for making the saliva fertility test convenient for women to utilize it on a daily basis during each menstrual cycle.

It is to be appreciated that the foregoing is a description of a preferred embodiment of the invention to which variations and modifications may be made without departing from the spirit and scope of the invention.

What is claimed is:

1. A fertility tester comprising
   a circular disc having a top, a bottom, a plurality of at least partially transparent regions concentrically disposed therealong, and a plurality of indicia corresponding to said transparent regions, each of which identifies day of woman's menstrual cycle,
   support means, on which said disc is rotatably mounted,
   masking means fixedly mounted relative to said support means and covering a portion of said disc thereby preventing viewing of some of said transparent regions, said masking means further having an opening through which at least one of said transparent regions is exposed for enabling a woman to place her saliva thereon, said disc being rotatable relative to said masking means whereby any one of said transparent regions may be exposed, and
   magnifier means mounted on said support means at viewing position for providing an enlarged view of the saliva on one of aid transparent regions, said masking means exposing the indicium corresponding to said one of said transparent regions both when it is at said opening and at said viewing position.

2. A fertility tester according to claim 5 further comprising illumination means mounted on said support means in alignment with said masking means opening for illuminating the saliva on said disc.

3. A fertility tester according to claim 1 wherein said support means comprises a housing, said disc being removably and rotatably mounted therein, and said masking means comprises a cover removably mounted on said housing whereby said cover partially masks said disc when said cover is mounted on said housing, and said disc can be removed from said housing when said cover is removed therefrom.

4. A fertility tester according to claim 3 wherein said housing comprises a circumferential ledge for supporting the outer circumference of the bottom of said disc.

5. A fertility tester according to claim 3 wherein said cover has a notch in its outer circumference defining said opening.

\* \* \* \* \*

UNITED STATES PATENT AND TRADEMARK OFFICE
CERTIFICATE OF CORRECTION

PATENT NO : 5,639,424
DATED : Jun. 17, 1997
INVENTOR(S): Rausnitz

It is certified that error appears in the above-identified patent and that said Letters Patent is hereby corrected as shown below:

In claim 1, at column 4, line 41, after "at" insert --a--;

line 43, change "aid" to --said--.

Signed and Sealed this

Second Day of March, 1999

Attest:

Q. TODD DICKINSON

*Attesting Officer*     *Acting Commissioner of Patents and Trademarks*